United States Patent [19]

McWilliams et al.

[11] Patent Number: 6,096,923
[45] Date of Patent: Aug. 1, 2000

[54] PROCESS FOR THE PREPARATION OF NITROSOUREA COMPOUNDS

[75] Inventors: Matthew P McWilliams; Chester Sapino, both of Sewell, N.J.

[73] Assignee: Johnson Matthey Public Limited Company, London, United Kingdom

[21] Appl. No.: 09/151,777

[22] Filed: Sep. 11, 1998

[30] Foreign Application Priority Data

Sep. 13, 1997 [GB] United Kingdom .................. 9719426

[51] Int. Cl.⁷ ................................................. C07C 275/68
[52] U.S. Cl. .............................................................. 564/33
[58] Field of Search .................................................. 564/33

[56] References Cited

U.S. PATENT DOCUMENTS

| | | | |
|---|---|---|---|
| 4,028,410 | 6/1977 | Yanko et al. .................... | 260/553 R |
| 4,128,639 | 12/1978 | Lin et al. ............................ | 424/180 |
| 4,367,239 | 1/1983 | Bregnedal et al. .................. | 424/322 |
| 4,423,076 | 12/1983 | Laki ..................................... | 424/322 |
| 5,001,158 | 3/1991 | Madelmont et al. ................ | 514/589 |

FOREIGN PATENT DOCUMENTS

| | | | | |
|---|---|---|---|---|
| 2 589 860 | 5/1987 | France | ...................... | C07C 135/00 |
| 1 469 381 | 4/1977 | United Kingdom | .......... | C07C 127/15 |

OTHER PUBLICATIONS

Lown et al, J.C.S. Chem. Comm., pp 675–676, 1981.

Kim et al, Arch. Pharm. Res., vol. 20, No. 3, pp 259–263, 1997.

Chemical Abstracts XP0020884888, 1974.

*Primary Examiner*—Shailendra Kumar
*Attorney, Agent, or Firm*—Pillsbury Madison & Sutro LLP

[57] ABSTRACT

A process for the preparation of a nitrosourea derivative, in particular 1,2-bis(2-chloroethyl)-1-nitrosourea, comprises reacting a non-nitrosated urea derivative with a metal nitrite in a two-phase solvent system comprising an aqueous acid and a non-miscible organic solvent.

8 Claims, No Drawings

PROCESS FOR THE PREPARATION OF NITROSOUREA COMPOUNDS

The present invention relates to a process for the preparation of a nitrosourea derivative, in particular 1,3-bis(2-chloroethyl)-1-nitrosourea.

Nitrosourea derivatives are well known for their antitumour properties and, since 1972, 1,3-bis(2-chloroethyl)-1-nitrosourea (BCNU) has been charted by the National Cancer Institute for use against brain tumours, colon cancer, Hodgkins disease, lung cancer and multiple myeloma. Improving the process for its preparation is therefore of great interest.

Previously-disclosed methods for preparing nitrosourea derivatives involve nitrosating the corresponding urea derivative using a homogeneous mixture of the urea derivative, the nitrosating agent and an aqueous acid. Various nitrosating agents have been used such as dinitrogen trioxide (U.S. Pat. No. 4,028,410), dinitrogen tetroxide (FR 2589860) and sodium nitrite in combination with aqueous acetic acid (U.S. Pat. No. 4,128,639).

The experience gained using these prior art methods for preparing nitrosourea derivatives show that they generally result in a relatively low yield. Additionally, the material isolated generally requires an additional purification step to achieve an acceptable product.

The present inventors have devised an improved process which results in a substantially pure product in a reproducibly good yield. Accordingly, the present invention provides a process for the preparation of a nitrosourea derivative, which process comprises reacting a non-nitrosated urea derivative with a metal nitrite in a two-phase solvent system comprising an aqueous acid and a non-miscible organic solvent.

More specifically, the process for the nitrosation of a urea derivative to form a nitrosourea derivative comprises the steps of:
(i) dissolving the urea derivative in aqueous acid;
(ii) adding to the solution resulting from step (i) a non-miscible organic solvent to form a two-phase reaction mixture;
(iii) adding a solution of a metal nitrite to the two-phase mixture, and if desired, isolating the nitrosourea derivative thereby prepared from the organic phase.

For example, and preferably, the isolation step is carried out by:
(iv) discarding the acidic aqueous layer, and washing and drying the organic phase.

Suitably, the metal nitrite is an alkali or alkaline earth metal nitrite, such as sodium nitrite, potassium nitrite, lithium nitrite, preferably sodium nitrite. Suitably, the aqueous acid is a mineral acid such as hydrochloric, hydrobromic, sulphuric, phosphoric and hypochloric, preferably sulphuric acid, more preferably 38% sulphuric acid.

The non-miscible organic solvent is one in which the non-nitrosated urea derivative is substantially insoluble but in which the nitrosated derivative is substantially soluble. Examples of suitable organic solvents are alkanes, cycloalkanes, alcohols, ketones, aldehydes, esters, aromatic hydrocarbons, chlorinated hydrocarbons and organic acids. Preferred solvents are chlorinated hydrocarbons, especially chlorinated alkanes such as methylene chloride.

The nitrosation process is suitably carried out at a non-extreme temperature of for example 0–50° C., suitably 5–25° C., preferably below room or ambient temperature, more preferably 5–15° C.

Suitably, the process is used for the preparation of nitrosourea derivatives of

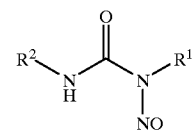

(I)

wherein $R^1$ and $R^2$ are the same or different and are each selected from substituted or unsubstituted hydrocarbon chains having from 1 to 10 carbon atoms. Suitably, the chains have 1 to 6 carbon atoms, preferably 2 to 3 carbon atoms and most preferably 2 carbon atoms. Preferably, the hydrocarbon chain is an optionally-substituted alkyl chain. The one or more substituents, when present, may be the same or different and are suitably selected from hydrocarbyl radicals, halo, ester, amide, carboxylic acid, ether, thioether and alcohol groups. Preferably, the substituents are selected from halo and most preferably are chloro.

Preferably, the process is used to prepare 1,3-bis(2-chloroethyl)-1-nitrosourea (BCNU).

The present invention further provides an improvement in a process for preparing a nitrosourea derivative, which process comprises reacting the corresponding non-nitrosated urea derivative with an alkali metal nitrite and an aqueous acid, the improvement comprising the addition of a non-miscible organic solvent, whereby a two-phase reaction mixture is formed from the organic phase of which the nitrosourea derivative is capable of being isolated in improved yield and of improved purity.

Preferably, the nitrosourea resulting from the product solution prepared according to the present invention (step (iv)) is then recrystallised from a suitable organic solvent or mixture of solvents. More preferably, the crystallisation step makes use of a solvent/anti-solvent system and overcomes the problems presented by the unusual solubility properties of nitrosourea derivatives. The crystallisation process is suitably carried out by chilling a sufficient volume of a suitable hydrocarbon anti-solvent. The nitrosourea is precipitated by metered addition of the dried product solution to the chilled anti-solvent. Suitable hydrocarbons for use as the anti-solvent include $C_{1-8}$ alkanes, preferably n-heptane.

The present invention will now be described by way of example only which is not intended to be limiting thereof.

For comparative purposes, an authentic sample of BCNU (carmustine) was obtained from a current manufacturer. For identification, $^1H$ NMR spectra were obtained for the authentic sample and samples from each of the examples described below. Deuterated chloroform was the solvent of choice for analysis. Tetramethylsilane was used as an internal standard to assign the chemical shifts of each signal. Also, peak areas were obtained by integration to verify the chemical structure of the materials.

The authentic sample displayed the folllowing signals of interest: a triplet @ 3.505 ppm (2), a multiplet @ 3.745 ppm (2), a multiplet @ 3.859 ppm (2), and a triplet @ 4.181 ppm (2). In addition, the spectra displayed a broad peak @ 7.26 ppm, accounted for by the amine proton in carmustine.

COMPARATIVE EXAMPLE 1

A solution was prepared of 2.0 g of 1,3-bis(2-chloroethyl)-1-urea (BCU) dissolved in 12 ml of 37% HCl, and chilled to 5–15° C. To this, a solution of 1.6 g of sodium nitrite in 14.4 ml of deionised water was added dropwise. After a two-hour agitation period, the aqueous mixture was extracted with 12 ml of methylene chloride. The aqueous portion was further extracted with an additional 5 ml of methylene chloride. After drying over sodium sulphate, the methylene chloride solution was stripped to a reddish/green oil. The solid was crystallised from a mixture of methyl tert-butyl ether and petroleum ether. Analysis, by NMR, of the product isolated from this preparation showed negligible levels of BCU. The reaction yielded ~35% of the theoretical yield.

COMPARATIVE EXAMPLE 2

A solution was prepared of 2.0 g of BCU dissolved in 12 ml of 38% $H_2SO_4$, and chilled to 5–15° C. To this, a solution of 1.6 g of sodium nitrite in 14.4 ml of deionsed water was added dropwise. After a two-hour agitation period, the aqueous mixture was extracted with 12 ml of methyl tert-butyl ether. The aqueous portion was further extracted with an additional 5 ml of methyl tert-butyl. After drying over sodium sulphate, the methyl tert-butyl solution was stripped to an oil. The solid was crystallised from a mixture of methyl tert-butyl ether and petroleum ether. Analysis, by NMR, of the product isolated from this preparation showed negligible levels of BCU. The reaction yielded ~50% of the theoretical yield.

EXAMPLE 1

A solution was prepared of 50.0 g of BCU dissolved in 500 ml of 38% $H_2SO_4$, and chilled to 5–15° C. To the sulphuric acid solution, 350 ml of methylene chloride added. To this two-phase mixture, a solution of 120.0 g of sodium nitrite in 600 ml of deionised water was added dropwise. After a brief agitation period, the layers were separated. The organic extract was washed with 350 ml of deionised water. After drying over sodium sulphate, the methylene chloride solution was stripped to an oil. The oil was redissolved in 115 ml of toluene. The solid was crystallised by addition of the toluene solution to chilled n-heptane. The reaction yielded ~75% of the theoretical yield. $^1$H NMR spectra were obtained using the conditions described above. This sample displayed the following signals of interest: a triplet @ 3.511 ppm (2), a multiplet @ 3.754 ppm (2), a multiplet @ 3.840 ppm (2), and a triplet @ 4.182 ppm (2). In addition, the spectra displayed a broad peak @ 7.26 ppm, accounted for by the amine proton in Carmustine. These data confirm the product as bis-chloroethyl nitrososurea (carmustine).

EXAMPLE 2

A solution was prepared of 20.0 g of BCU dissolved in 200 ml of 38% $H_2SO_4$, and chilled to 5–15° C. To the sulphuric acid solution, 60 ml of methylene chloride and 80 ml of n-heptane were added. To this two-phase mixture, a solution of 32.0 g of sodium nitrite in 160 ml of deionised water was added dropwise. After a brief agitation period, the layers were separated. The organic extract was washed with 50 ml of deionised water. The organic solution was dried over sodium sulphate. The solid was crystallised by addition of the product solution to chilled n-heptane. The reaction yielded ~63% of the theoretical yield. $^1$H NMR spectra were obtained using the conditions described above. This sample displayed the following signals of interest: a triplet @ 3.506 ppm (2), a multiplet @ 3.750 ppm (2), a multiplet @ 3.836 ppm (2), and a triplet @ 4.181 ppm (2). In addition, the spectra displayed a broad peak @ 7.26 ppm, accounted for by the amine proton in Carmustine. These data confirm the product as bis-chloroethyl nitrososurea (carmustine).

In addition, the authentic sample and example samples were analysed by HPLC. The identification of the example samples as bis-chloroethyl nitrosourea (Carmustine) was confirmed by comparison of HPLC retention times.

We claim:

1. A process for the preparation of 1,3-bis(2-chloroethyl)-1-nitrosourea which process comprises reacting 1,3-bis(2-chloroethyl)-1-urea with a metal nitrite in a two-phase solvent system comprising aqueous sulphuric acid and a non-miscible chlorinated hydrocarbon solvent.

2. A process according to claim 1, wherein the non-miscible solvent is one in which the 1,3-bis(2-chloroethyl)-1-urea is substantially insoluble but in which the 1,3-bis(2-chloroethyl)-1-nitrosourea is substantially soluble.

3. A process according to claim 1, wherein the non-miscible chlorinated hydrocarbon solvent is methylene chloride.

4. A process according to claim 1, carried out at a temperature in the range of from 0 to 50° C.

5. A process according to claim 1, carried out at a temperature in the range of from 5 to 15° C.

6. A process according to claim 1 for the preparation of 1,3-bis(2-chloroethyl)-1-nitrosourea, which process comprises the steps of:

(i) dissolving 1,3-bis(2-chloroethyl)-1-urea in an aqueous acid;

(ii) adding to the solution resulting from step (i) the non-miscible solvent to form a two-phase reaction mixture;

(iii) adding a solution of the metal nitrite to the two-phase mixture; and optionally, isolating the 1,3-bis(2-chloroethyl)-1-nitrosourea thereby prepared from the organic phase.

7. A process according to claim 6 further comprising the step of:

(iv) discarding the acidic aqueous layer, and washing and drying the organic phase.

8. A process according to claim 6 or claim 7 further comprising the step of:

(v) precipitating the nitrosourea by metered addition of the dried product solution from step (iv) to a chilled hydrocarbon solvent.

* * * * *